United States Patent [19]

Curtis

[11] 4,418,138

[45] Nov. 29, 1983

[54] PHOTOPOLYMERIZABLE MATERIALS FOR USE IN PRODUCING STENCILS FOR SCREEN PRINTING

[75] Inventor: John R. Curtis, Thanet, England

[73] Assignee: Sericol Group Limited, London, England

[21] Appl. No.: 411,565

[22] Filed: Aug. 25, 1982

[30] Foreign Application Priority Data

Nov. 3, 1981 [GB] United Kingdom ............... 8133114

[51] Int. Cl.³ .................. G03C 1/68; G03C 500/00
[52] U.S. Cl. .................................. 430/253; 430/281; 430/286; 430/283; 430/308; 430/922; 204/159.23; 204/159.24
[58] Field of Search ............ 430/915, 922, 281, 921, 430/286, 308, 253; 549/27; 204/159.24

[56] References Cited

U.S. PATENT DOCUMENTS 3,926,643 12/1975 Chang ........................... 430/922 X
4,385,182 5/1983 Fischer et al. .................... 549/27

FOREIGN PATENT DOCUMENTS 2095248 9/1982 United Kingdom ............... 549/27

*Primary Examiner*—John E. Kittle
*Assistant Examiner*—C. Hamilton
*Attorney, Agent, or Firm*—Cushman, Darby & Cushman

[57] ABSTRACT

Aqueous compositions useful in making stencils for screen printing comprise one or more unsaturated monomers, a tertiary amino compound, a colloid, and a water-soluble, carboxy- or sulpho-alkyleneoxy-thioxanthone photoinitiator. When coated on to a suitable support sheet and dried, photosensitive sheets are obtained useful for making stencils for screen printing by the direct, indirect, or direct/indirect methods.

18 Claims, No Drawings

PHOTOPOLYMERIZABLE MATERIALS FOR USE IN PRODUCING STENCILS FOR SCREEN PRINTING

DESCRIPTION

This invention relates to photopolymerisable materials for use in screen printing.

In screen printing, three main photosensitive stencil systems are used: in the first, the so-called indirect method, a photosensitive composition is coated on to a transparent polymeric backing support, usually of a polyester. The coated sheet can be irradiated with actinic light through a positive transparency after which, depending on the type of photopolymerisation system used, the film can be developed with water, or activated with a per-compound and then developed with water. The wet image on its polymeric backing support is then adhered to the screen mesh by application of gentle even pressure, and after drying, the polymeric support sheet is removed, leaving the photopolymerised image on the screen mesh ready for printing.

In the second system, the so-called direct method, a stencil image is produced on a screen mesh by photosensitising a water-soluble crosslinkable colloid with a suitable photocrosslinker which can be a dichromate compound or a polymeric diazonium salt, and then coating the colloid on to the screen mesh. When sensitised in this manner the coated layer on the screen mesh, after drying, can be exposed to actinic light through a suitable positive transparency to produce a latent image. On development of the image with water, the areas irradiated by the actinic light remain as they have become insoluble in water, while the areas protected from the actinic light, which still retain the original water solubility of the water-soluble colloid, are washed away to leave an image which, after drying, is ready for printing.

In the third system, the so-called direct/indirect method, a stencil image is produced from an unsensitised layer on a polymeric backing support which is laid with the layer in contact with the screen mesh. A layer photosensitised by the previously described methods is applied to the mesh and wets the unsensitised layer on its polymeric backing support. After drying, the backing support is stripped off and the dry emulsion remaining on the screen is exposed and developed in the previously described manner.

All three methods of producing stencil images on a screen mesh have serious drawbacks. In the first method, the system has, when the process relies on photoinitiators of the ferric salt type, to undergo a treatment with a pre-compound, e.g. hydrogen peroxide, to cause free radicals to be formed which initiate photopolymerisation of the monomers present and cause insolubilisation of the layer. After this activation step, normal water development follows to give the image. Alternatively the indirect method relies on a leuco sulphuric ester of an indigo or thio-indigo dye as the photoinitiator which requires the presence of moisture to remain active. This necessitates the use of quite large quantities of humectants in the formulation so that the material will function correctly in hot dry climates. These humectants create problems in high humidity areas and can cause reticulation of the film when it is removed from its sealed container. Their presence also tends to reduce the mechanical strength of the carrier colloid (usually polyvinyl alcohol), resulting in shorter print runs with the finished stencil.

The direct system suffers the drawback that the material is usually of a Two Pack variety which requires both a sensitiser and a base emulsion which on sensitising has a useful pot life of a matter of days when the sensitiser is a dichromate and a maximum of three months when the sensitiser is a polymeric diazo salt. The direct/indirect system obviously suffers the same drawbacks as the direct method.

Another disadvantage in the above methods for producing stencil images on a screen is that after exposure there is very little contrast between the exposed and unexposed areas so that there is no satisfactory way of inspecting the image before the development stage. This means that if the art work is faulty, or the positioning of the positive is incorrect, the fault goes unnoticed until after the final stencil image has been produced.

This present invention is based upon the discovery that a novel water-soluble photoinitiator, having a useful absorption at 395 nm combined with solubility in water of a suitable pH, can be used as an initiator for effecting the polymerisation of vinyl and acrylic monomers in aqueous solution or in coated dry layers. Materials using this initiating system are particularly suited to the screen printing process as the useful absorption maximum of these initiators corresponds well with the main useful output wavelengths of the mercury lamps commonly used in the screen printing stencil-making process. Compositions containing the novel photoinitiator do not suffer the drawback of requiring an activation step by addition of a solution of a peroxide or equivalent substance, or the disadvantage of having to contain quite large quantities of humectant. In solution form they do not require sensitisation, and so can provide the convenience and simplicity of a one pack system.

In a preferred embodiment of the invention the coating is coloured in such a way that after exposure there is an easily visible colour difference between the exposed and the non-exposed areas. The production of a visible and highly contrasted latent image immediately upon exposure to actinic light enables the stencil maker in the process of exposing a number of screen stencils at about the same time to know whether a given screen has been exposed or not. For instance, if his work is interrupted, or where a large single stencil screen is exposed a number of times, for example in the so-called 'step and repeat process' of preparing screen printing stencils, the operator is able to ascertain immediately which areas have been exposed. Also, where multiple exposures are required, the visible image of the first exposure may act as a guide for registration of subsequent exposures.

A photosensitive emulsion, applied to a screen mesh in any of the aforementioned methods, which is capable of producing a visible image upon exposure, prior to any subsequent development of treatment thereof, has also the advantage of vividly showing up screens that have been exposed by accident ("fogged" by exposure to stray sunlight or artificial light).

According to the present invention, an aqueous photosensitive composition for the preparation of printing screens comprises one or more terminally ethylenically unsaturated monomers, which are dispersible, miscible or soluble in water, one or more tertiary nitrogen-containing monomers optionally containing terminal ethylenic unsaturation as accelerators, a water-soluble colloid, and a water-soluble photoinitiator of the formula:

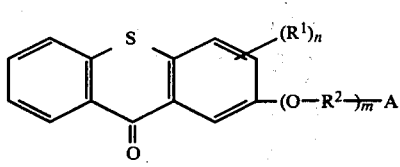

where $R^1$ is halogen, alkyl, alkoxy, alkylthio, nitro, amino, alkylamino, dialkylamino, hydroxyalkylamino, alkanoylamino, benzoylamino, N-alkanoyl-N-benzoylamino, sulphonamido or acetyl, $R^2$ is alkylene of 1 to 4 carbon atoms, n is 0, 1 or 2, m is 1 or 2, and A is —COOH, —SO$_3$H, —OSO$_3$H, or —OCO-X-COOH (where X is such that HOOC-X-COOH is a di- or tricarboxylic acid of up to 8 carbon atoms), the aforesaid alkyl, alkoxy, and alkanoyl residues containing up to 4 carbon atoms each, or a water-soluble salt thereof. Such photoinitiators are used in the new compositions in a proportion of 0.1 to 5%, and preferably 0.12 to 1.8% by weight. When A is carboxy it may be necessary to convert part or all of the photoinitiator into a salt to assure sufficient water-solubility. Certain of the aforesaid thioxanthones are novel compounds described and claimed in our application Ser. No. 411,570 filed on even date herewith and entitled "Water-soluble Thioxanthone Photoinitiators".

Preferred photoinitiators of the aforesaid formula are 2-(carboxymethoxy)-thioxanthone, 2-(3-carboxypropoxy)-thioxanthone, 2-(3-sulphopropoxy)-thioxanthone, 2-(2-sulphoethoxyethoxy)-thioxanthone, 2-(3-sulphopropoxy)-3,4-dimethylthioxanthone, each as free acid or as a water-soluble salt thereof.

The aforesaid photoinitiators may be made by condensation of orthomercapto-benzoic acid with a phenol of the formula:

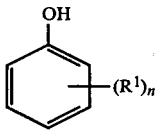

where $R^1$ and n are as hereinbefore defined and the 4 position of the ring is unsubstituted, in the presence of sulphuric acid as catalyst, followed by reaction of the product obtained with a halo-aliphatic acid, acid salt, or acid ester of formula Hal-$R^2$-(O-$R^2$)$_{m-1}$-$A^1$ where Hal is halogen, $R^2$ is as hereinbefore defined and $A^1$ is a radical A as aforesaid or an esterified such radical, or salt thereof, followed by hydrolysis of any ester group present.

According to a feature of the invention an image printing screen may be produced by subjecting to imagewise exposure a light-sensitive material comprising a base support coated with a composition as aforesaid and dried, and then removing, e.g. by dissolution in water, the unexposed parts of the coating, the insolubilised parts of the coating being either formed on, or transferred to, the printing screen.

The terminally ethylenically unsaturated monomers must contain at least one non-aromatic polymerizable double bond between adjacent carbon atoms, and be water-dispersible, -miscible or -soluble. The total proportion of such monomer or monomers should be 4 to 30% by weight of the composition, preferably 6–15% by weight. Monofunctional monomers, especially vinyl and acrylic monomers, may be used, e.g. acrylamide, methacrylamide, N-methylolacrylamide, or N-vinyl-pyrrolidone, in a proportion of 2 to 10%, preferably 3 to 8%, by weight of the composition. In order to increase the efficiency of the process, however, the cross-linking density is preferably increased, to provide a greater degree of cross-linking in a shorter exposure time, by including in the composition one or more polyunsaturated vinyl or acrylic compounds which are water-dispersible, water-soluble or water-miscible but which contain two or more terminal polymerizable ethylenically unsaturated groupings per molecule. Suitable such compounds are N,N'-methylene-bis-acrylamide, N,N'-trimethylene-diacrylamide, N,N'-hexamethylene-diacrylamide, polyethylene glycol 200 diacrylate, triethylene glycol diacrylate, tripropylene glycol diacrylate, and tetraethylene glycol diacrylate. These compounds may be used alone or in admixture, generally in a proportion of 0.3 to 15%, preferably 0.5 to 9%, by weight of the composition. Generally speaking, such compounds increase the degree of cross-linking and increase the hardness of the polymer obtained. Trifunctional terminally ethylenically unsaturated compounds can also be included to increase the cross-linking density, hardness and speed of the composition. However such compounds are kept to a low level (usually 0 to 4.0%, and preferably 0 to 2%, by weight of the total composition). They should be dissolved in the water soluble/miscible monomers before dispersion of the latter in the water-soluble colloid. Suitable trifunctional cross-linking monomers are trimethylolpropane triacrylate and pentaerythritol triacrylate.

To increase the photosensitivity still further, it is necessary to add a tertiary nitrogen-containing compound, normally in a proportion of 0.7 to 6%, and preferably 1 to 4%, by weight of the composition. Compounds of this kind, e.g. triethanolamine, methyldiethanolamine, ethyl-diethanolamine, N,N-dimethylaminoethyl acrylate, N,N-diethylaminoethyl acrylate and Uvecryl P101 (UCB), behave as secondary initiators or accelerators for the primary photoinitiator and increase the efficiency and speed of the cross-linking action.

The composition can contain a cationic surfactant and the preferred surfactant contains one or two tertiary substituted nitrogen atoms and sufficient polyoxyethylene or polyoxypropylene residues to confer the degree of water-solubility required. Dialkyl-polyoxyethylene amines are, for example, suitable. They are able to solubilise and stabilise the novel photoinitiator which, especially if in the carboxy form and solubilised with simpler organic bases, can precipitate from the system and become inactive. The preferred surfactants are the Catofor family (ABM chemicals) and specifically Catofor 06. The proportion of surfactant is normally 0 to 5%, and especially 0 to 3%, by weight of the composition.

Suitable water-soluble colloids include polyvinyl alcohol, gelatin, hydroxyethyl-cellulose, hydroxpropyl-cellulose and polyvinyl-pyrrolidone. Such colloid carriers are not insolubilised by the new photoinitiators in the absence of the unsaturated monomer. The compositions of the invention normally contain 4 to 14%, and preferably 6 to 10%, by weight of the composition.

It is preferred to include in the composition of the invention an inert polymer emulsion of, e.g. a vinyl acetate homopolymer or copolymer, in order to aid adhesion, strength and durability of the polymerized coating. The proportion of such an emulsion (based on its solids content) may be up to 30% of the weight of the composition, and is preferably 5 to 15%. A plasticizer, e.g. dibutyl phthalate, may also be added in a proportion up to 5% but preferably only 0 to 3%, by weight of the composition, to improve the flexibility of the exposed composition.

The photosensitive composition may also contain colorants, e.g. dyes or pigments, in a proportion up to 1% by weight to render the final image visible. The initial coating can be coloured to provide visible images or the photopolymerised layer can be treated with a colouring solution after processing. In this connection it is especially preferred to include in the new compositions a thioindigoid or indigoid dyestuff, e.g. of the Anthrasol series (Hoechst). Such dyestuffs have the valuable property mentioned above that, in the presence of the free radical photoinitiator and a suitable water-soluble plasticiser for the water-soluble colloid, they change colour on exposure to actinic light to produce a clearly visible contrast between the light-struck and non-light-struck area. Such dyestuffs have the additional advantage of acting as an additional photoinitiator (provided at least the dried composition contains sufficient moisture).

A filler such as silica, starch, kaolin, or titanium dioxide, may also be included in the composition, e.g. in a proportion up to 20%, and preferably 5 to 12%, by weight of the composition, to increase the solids content of the formulation and reduce surface stickiness.

The compositions of the present invention are aqueous and may contain 40 to 80% by weight of water, but preferably 50 to 70% by weight, including water added in admixture with other ingredients, e.g. the water in any polymer emulsion included in the composition. A minor amount up to 8% of other solvents, e.g. ethanol, may be aded to improve the compatibility of the composition, e.g. 3 to 6% by weight of the composition.

In use the new compositions are coated on to a suitable support, e.g. a printing screen or a flexible transparent film and dried. The coating is then exposed to actinic light to form the desired image.

The actinic radiation used to expose the new compositions may be natural sunlight or light derived from a carbon arc lamp, a xenon arc lamp, a high intensity mercury lamp or a tungsten filament light. The exposed layer is then developed, e.g. with water, to remove unexposed composition.

The images formed by photo-polymerisation of the compositions described above can be used for preparing stencils for screen printing either by the direct or indirect method, or in any photographic or photomechanical process where resist, stencils or relief images are required, for example etching resists for printing plates, name plates, dials and circuit patterns, ink accepting images for lithographic masters or negative stencils for positive reversal litho systems. Images can also serve as dye resists or printing matrices as well as visually coloured displays in reflective or transparent form. The suitability of the image for a specific application is determined primarily by the choice of colloid and/or unsaturated monomer components.

The following Examples illustrate the invention.

EXAMPLE I

The following soluton was coated on to a transparent presubbed polyester film base:

|  | Parts by Weight |
| --- | --- |
| Catofor 06 (ABM Chemicals)[1] | 1.0 |
| 15% aqueous solution GM14L (Gohsenol)[2] | 50.0 |
| Dimethylaminoethyl acrylate | 3.0 |
| Polyethylene glycol 200 diacrylate | 7.0 |
| Trimethylol-propane triacrylate | 1.0 |
| Vinamul 8440 Emulsion[3] | 25.0 |
| 2-(Carboxymethoxy)thioxanthone | 0.5 |
| Anthrasol Pink 1R | 0.5 |
| Polyethylene glycol 200 | 1.0 |

[1] Catofor 06 is a cationic surfactant containing a tertiary amino group and 6 ethylene oxide residues per molecule.
[2] Gohsenol GM14L is a medium molecular weight 88% hydrolysed (12% residual acetate) polyvinyl alcohol.
[3] Vinamul 8440 emulsion is a polyvinyl acetate homopolymer emulsion having a solids content of 56% by weight obtainable from Vinyl Products Ltd., Carshalton, Surrey, England.

The coating was dried and exposed through a photographic positive transparency to a 800 watt mercury halide (Thorn) lamp at a distance of 1 meter for 120 seconds. The latent image was visible as cream-yellow on a pink background. After washing with cold water (15° C.) a pigmented relief image was obtained.

When the unsaturated monomers were excluded from the system no insolubilisation of the colloid binder was obtained. This has been demonstrated by making up and coating the following solution.

|  | Parts by Weight |
| --- | --- |
| Catofor 06 (ABM Chemicals)[1] | 1.0 |
| 15% solution GM14L (Gohsenol)[2] | 50.0 |
| Vinamul 8440 Emulsion[3] | 25.0 |
| 2-(Carboxymethoxy)thioxanthone | 0.5 |
| Anthrasol Pink 1R | 0.5 |
| Polyethylene glycol 200 | 1.0 |

The coating was dried and exposed to a 800 W mercury halide lamp at a distance of 1 meter for 12 minutes. On washing with water the whole coated layer was removed. This indicates that no insolubilisation of the layer occurs in the absence of an unsaturated monomeric compound.

EXAMPLE II

|  | Parts by Weight |
| --- | --- |
| Catofor 06 (ABM Chemicals)[1] | 1.0 |
| 2-(Carboxymethoxy)thioxanthone | 0.5 |
| Ethanol | 5.0 |
| Polyethylene glycol 200 diacrylate | 10.5 |
| N—Vinyl-pyrrolidone | 4.5 |
| Uvecryl P101 (UCB)[4] | 2.0 |
| 20% Gohsenol KP08 solution[5] | 50.0 |
| Anthrasol Blue-Black 1RD | 0.5 |
| Polyethylene glycol 200 | 1.0 |

[4] Uvecryl P101 is an unsaturated copolymerizable amino group-containing monomer from UCB SA (Drogenbos Belgium).
[5] Gohsenol KP08 is a low viscosity polyvinyl alcohol with 25–29% of residual acetate groups from Nippon Gosei (Osaka, Japan).

The above formulation was coated on a polyester filament screen mesh. The formulation was applied with a coating trough and a coat was given to each side of the mesh. After drying, the material was exposed through a positive transparency to a 800 watt mercury halide lamp at the distance of one meter for 2½ minutes. The latent image was visible as cream on a grey-green background. After washing with cold water, a good visible stencil image was obtained.

EXAMPLE III

| | Parts by Weight |
|---|---|
| Catofor 06 (ABM Chemicals)[1] | 3.5 |
| 2-(Carboxymethoxy)thioxanthone | 2.5 |
| N—Vinyl-pyrrolidone | 26.0 |
| Polyethylene glycol 200 diacrylate | 39.0 |
| Trimethylol-propane triacrylate | 9.0 |
| Uvecryl P101 (UCB)[4] | 5.0 |
| Kaolin | 35.0 |
| Gohsenol KP08 25% soln.[5] | 270.0 |
| Triton GR5M 10% soln. (surfactant) | 2.0 |
| Dibutyl phthalate | 10.0 |
| Anthrasol Pink 1R | 1.2 |
| Polyethylene Glycol 200 | 3.0 |

The above composition was coated on to a sheet of pre-subbed polyester and exposed through a film positive transparency for 45 seconds to a 800 watt mercury halide lamp at a distance of 1 meter. The latent image was visible as cream on a pink background. After washing with cold water (15° C.), a relief image was obtained.

EXAMPLE IV

| | Parts by Weight |
|---|---|
| 13% aqueous solution of GH20 (Gohsenol)[6] | 50.0 |
| Methylene Bis Acrylamide | 0.5 |
| Acrylamide | 5.0 |
| Triethanolamine | 0.9 |
| 2-(3-Sulphopropoxy thioxanthone) | 0.1 |
| Vinnapas EP14[7] (Wacker) | 10.5 |
| 50% Irgalite Blue CPV2[8] (Ciba Geigy) | 0.4 |

The above formulation was coated on a 120 threads/cm polyester screen mesh dried and exposed through a positive transparency to a 800 watt mercury halide lamp at a distance of one meter for 10 seconds. After washing with cold water, a good visible stencil image was obtained.

EXAMPLE V

| | Parts by Weight |
|---|---|
| 13% aqueous solution of GH20 (Gohsenol)[6] | 50.0 |
| Methylene Bis acrylamide | 0.5 |
| Acrylamide | 5.0 |
| Triethanolamine | 1.0 |
| 2(2 Sulphoethoxyethoxy) thioxanthone | 0.1 |
| Vinnapas EP14[7] (Wacker) | 10.5 |
| Kaolin | 6.0 |
| 50% Irgalite Blue CPV2[8] (Ciba Geigy) | 0.4 |

The above formulation was coated on to a 120 threads/cm polyester screen mesh and exposed through a positive transparency to a 800 watt Mercury halide lamp at a distance of one meter for two seconds. After washing with cold water, a good stencil image was obtained.

EXAMPLE VI

| | Parts by Weight |
|---|---|
| 13% aqueous solution of GH20[6] (Gohsenol) | 50.0 |
| Methylene Bis acrylamide | 0.5 |
| Acrylamide | 3.0 |
| Polyethylene glycol 200 Diacrylate[9] (Diamond Shamrock UK) | 2.0 |
| Triethanolamine | 1.0 |
| 2(3 Sulphopropoxy), 3,4 DiMethyl Thioxanthone | 0.1 |
| Vinnapas EP14[7] (Wacker) | 10.5 |
| 50% Irgalite Blue CPV2[8] (Ciba-Geigy) | 0.4 |

[6]Gohsenol GH20, trade name for a medium/high molecular weight polyvinyl alcohol supplied by Nippon Gohsei.
[7]Vinnapas EP14, a polyvinyl acetate/ethylene copolymer emulsion of approx. 55% solids, supplied by Wacker.
[8]Irgalite Blue CPV2, pigment paste for water-based formulations supplied by Ciba Geigy.
[9]Polyethylene glycol 200 Diacrylate. Difunctional acrylate supplied by Diamond Shamrock UK Ltd.

The above formulation was coated on to a 150 threads/cm polyester screen mesh and exposed through a positive transparency to a 800 watt mercury halide lamp at a distance of one meter for two seconds. After washing with cold water, a good stencil image was obtained.

The following Examples describe how the novel thioxanthone photoinitiators may be prepared.

EXAMPLE 1

Concentrated sulphuric acid (300 ml) was slowly added to thiosalicylic acid (30.9 g) and the mixture was stirred for 5 minutes to ensure thorough mixing. Phenol (94 g) was added slowly to the stirred mixture over a period of 30 minutes. After the addition, the mixture was stirred at room temperature for 1 hour, then at 80° C. for two hours, after which it was left to stand at room temperature overnight. The resulting mixture was poured carefully with stirring into 10 times its volume of boiling water which was then boiled for a further 5 minutes. The solution was cooled and filtered. The residue was recrystallised from acetone to give 2-hydroxythioxanthone as a yellow product.

2-Hydroxy-thioxanthone (4.56 g) was mixed with dimethylformamide (125 ml), ethyl 4-chlorobutyrate (6.02 g), potassium carbonate (2.80 g) and potassium iodide (0.50 g) and the mixture was stirred under reflux for four hours. The resulting mixture was poured carefully with stirring into cold distilled water. The yellow solid which precipitated, which is the ethyl ester of 2-(3-carboxypropoxy)thioxanthone, was collected by filtration and recrystallised from ethanol. The ethyl ester of 2-(3-carboxy-propoxy)thioxanthone (4.2 g) was dissolved in triethanolamine (50 ml) and a solution of potassium hydroxide (5.0 g) in distilled water (5 ml) and ethanol (20 ml) was slowly added with stirring. The resulting mixture was stirred under reflux for two hours, cooled, poured into a large excess of distilled water, and then acidified with hydrochloric acid. The resulting yellow precipitate was filtered off and recrystallised from ethanol to give 2-(3-carboxy-propoxy)thioxanthone.

EXAMPLE 2

2-Hydroxy-thioxanthone (11.40 g) and toluene (125 ml) were mixed and stirred and sodium methoxide (2.97 g) was added thereto portionwise and slowly. The temperature was slowly raised to boiling and the mixture stirred at that temperature for 1 hour. The thioxanthone changed colour from yellow to red indicating conversion to the sodium salt. The reaction mixture was cooled and filtered, and the residue was washed with ether and dried.

1-Chloro-3-bromopropane (104.0 g) ethanol (250 ml), and water (90 ml) were stirred under reflux, and a solution of sodium sulphite (25.0 g) in distilled water (90 ml) was added to the stirred refluxing reaction mixture over a period of two hours. After the addition, refluxing was continued for a further 2 hours after which the excess alcohol and 1-chloro-3-bromopropane were removed by distillation. The remaining aqueous solution was evaporated to dryness on a steam bath and the product was recrystallised from alcohol to yield sodium 3-chloro-propane-sulphonate as a white crystalline solid.

The sodium salt of 2-hydroxy-thioxanthone (8.6 g), sodium 3-chloro-propane-sulphonate (6.6 g) and dimethyl formamide (150 ml) were stirred under reflux for 2 hours. The resulting mixture was cooled and poured into a large excess of acetone. The solid was collected and recrystallised from methanol to give the sodium salt of 2-(3-sulphopropoxy)thioxanthanone.

EXAMPLE 3

Bis(2-chloroethyl)ether (94.4 g), ethanol (250 ml) and water (90 ml) were stirred together under reflux, and a solution of sodium sulphite (25.0 g) in distilled water (90 ml) was added to the stirred, refluxing reaction mixture over a period of 2 hours. After the addition, refluxing was continued for two hours after which time the excess alcohol and bis(2-chloro-ethyl) ether were removed by distillation. The remaining aqueous solution was evaporated to dryness on a water bath to give a white crystalline solid, which was stirred with diethyl ether and filtered to yield sodium 2-chloroethoxyethyl sulphonate.

The sodium salt of 2-hydroxythioxanthone (22.5 g), sodium 2-chloroethoxyethyl sulphonate (20.8 g), and dimethyl formamide (250 ml) were stirred together under reflux for 1 hour. The resulting mixture was cooled and poured into a large excess of acetone. The yellow precipitate was filtered off and recrystallised from boiling methanol to give the sodium salt of 2-(2-sulphoethoxyethoxy)thioxanthone.

EXAMPLE 4

1,4-Dibromo-butane (142.5 g), ethanol (250 ml) and water (90 ml) were stirred together under reflux. A solution of sodium sulphite (25.0 g) and distilled water (90 ml) was added to the stirred, refluxing reaction mixture over a period of two hours. After the addition, refluxing was continued for two hours, after which the excess ethanol and 1,4-dibromobutane were removed by distillation. The remaining aqueous solution was evaporated to dryness on the steam bath, and the residue was slurried with ether, filtered and dried to give sodium 4-bromo-butane sulphonate.

Sodium 4-bromobutane sulphonate (15.5 g), the sodium salt of 2-hydroxy thioxanthone (15.0 g), and dimethyl-formamide (200 ml) were stirred under reflux for two hours. The resulting mixture was cooled and poured with stirring into 600 ml of acetone. The precipitated solid was collected by filtration and recrystallised from boiling methanol to give the sodium salt of 2-(4-sulphobutoxy)thioxanthone.

EXAMPLE 5

Concentrated sulphuric acid (300 ml) was slowly added to thiosalicylic acid (30.9 g) and the mixture was stirred for 5 minutes to ensure thorough mixing. To the stirred mixture was added slowly over a period of 30 minutes 2,3-dimethyl-phenol (138 g). After the addition, the mixture was stirred at room temperature for 1 hour, and then at 80° C. for 2 hours, after which it was left to stand at room temperature overnight. The resulting mixture was poured carefully with stirring into 10 times its volume of boiling water after which it was boiled for a further five minutes, cooled, and filtered. The residue was recrystallised from acetone to give 2-hydroxy-3,4-dimethyl-thioxanthone as a yellow product.

2-Hydroxy-3,4-dimethyl-thioxanthone (10.2 g), and 5 M sodium hydroxide solution (150 ml) were stirred and heated together until the yellow colour had completely changed to red. The reaction mixture was cooled and filtered. The residue was washed with acetone and dried to give the sodium salt of 2-hydroxy-3,4-dimethyl-thioxanthone.

The sodium salt of 2-hydroxy-3,4-dimethylthioxanthone (6.5 g), sodium 3-chloro-propane-sulphonate (4.3 g) and dimethylformamide (150 ml) were stirred under reflux for 4 hours. The resulting mixture was cooled and poured into a large excess of acetone. The solid was separated and recrystallised from methanol to give the sodium salt of 2-(3-sulphopropoxy)-3,4-dimethylthioxanthone.

I claim:

1. An aqueous photopolymerisable composition comprising (1) at least one terminally ethylenically unsaturated monomer, which is dispersible, miscible or soluble in water, (2) at least one tertiary nitrogen-containing compound as accelerator, (3) a water-soluble colloid, and (4) a water-soluble photoinitiator of the formula:

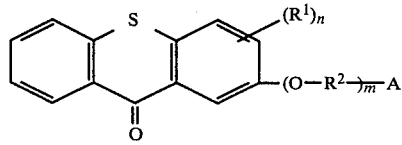

where $R^1$ is halogen, alkyl, alkoxy, alkylthio, nitro, amino, alkylamino, dialkylamino, hydroxyalkylamino, alkanoylamino, benzoylamino, N-alkanoyl-N-benzoylamino, sulphonamido or acetyl, $R^2$ is alkylene of 1 to 4 carbon atoms, n is 0, 1 or 2, m is 1 or 2, and A is —COOH, —SO$_3$H, —OSO$_3$H, or —OCO-X-COOH (where X is such that HOOC-X-COOH is a di- or tricarboxylic acid of up to 8 carbon atoms), the aforesaid alkyl, alkoxy, and alkenyl residues containing up to 4 carbon atoms each, or a water-soluble salt thereof.

2. A composition according to claim 1 wherein the monomer (1) comprises at least one terminally ethylenically mono-unsaturated monomer, and at least one terminally ethylenically di- or tri-unsaturated monomer as cross-linking agent.

3. A composition according to claim 2, wherein the mono-unsaturated monomer is selected from the class consisting of acrylamide, N-methylolacrylamide, methacrylamide and N-vinyl-pyrrolidone.

4. A composition according to claim 2, wherein the di- or tri-unsaturated monomer is selected from the class consisting of polyethylene glycol (200) diacrylate, triethylene glycol diacrylate, tripropylene glycol diacrylate, tetraethylene glycol diacrylate, N,N'-methylene-bis-acrylamide, N,N'-trimethylene-bis-acrylamide, N,N'-hexamethylene-bis-acrylamide, trimethylol-propane triacrylate, and pentaerythritol triacrylate.

5. A composition according to claim 1, wherein the said accelerator (2) is selected from the class consisting of triethanolamine, methyl-diethanolamine, ethyl-diethanolamine, N-N-dimethylamino-ethyl acrylate, N,N-diethylaminoethyl acrylate and Uvecryl P101.

6. A composition according to claim 1, wherein the said colloid (3) is selected from the class consisting of polyvinyl alcohol, polyvinylpyrrolidone, gelatin, hydroxyethyl-cellulose, and hydroxypropylcellulose.

7. A composition according to claim 1, wherein the said photoinitiator (4) is selected from the class consisting of 2-(carboxymethoxy)-thioxanthone, 2-(3-carboxypropoxy)-thioxanthone, 2-(3-sulphopropoxy)-thioxanthone, 2-(2-sulphoethoxyethoxy)-thioxanthone, 2-(3-sulphopropoxy)-3,4-dimethylthioxanthone, as the free acids and their water-soluble salts.

8. A composition according to claim 1, which also contains a cationic surfactant selected from the class consisting of polyoxyethylene and polyoxypropylene compounds containing at least one tertiary nitrogen atom per molecule.

9. A composition according to claim 1, which also contains an inert polymer emulsion.

10. A composition according to claim 1, which also contains a colouring agent and/or a filler.

11. A composition according to claim 1, which also contains a thioindigoid or indigoid dyestuff as colouring agent.

12. A composition according to claim 1, comprising, by weight of the said composition, 40 to 80% of water, 4 to 30% of the terminally ethylenically unsaturated monomer (1), 0.7 to 6% of the tertiary nitrogen-containing compound (2), 4 to 14% of the colloid (3), 0 to 5% of a cationic surfactant, and 0.1 to 5% of the said photoinitiator (4).

13. A composition according to claim 12 comprising, by weight of the said composition, 50 to 70% of water, 3 to 8% of monofunctional terminally ethylenically unsaturated monomer (1), 0.5 to 9% of di-functional terminally ethylenically unsaturated monomer (1), 0 to 2% of trifunctional terminally ethylenically unsaturated monomer (1), 1 to 4% of tertiary nitrogen-containing compound (2), 6 to 10% of colloid (3), 5 to 15% (based on solids content) of a polymer emulsion, 0 to 3% of a cationic surfactant, 5 to 12% of a filler, 0 to 3% of a plasticizer, and 0.12 to 1.8% of the photoinitiator (4).

14. A support sheet coated with a composition according to claim 1 and dried.

15. A screen for screen printing coated with a composition according to claim 1 and dried.

16. A transparent flexible support sheet coated with a composition according to claim 1 and dried.

17. A method of producing a stencil for screen printing which comprises irradiating a coated sheet as claimed in claim 16 with actinic light, developing the irradiated sheet and transferring the insolubilised image to a screen.

18. A method of producing a stencil for screen printing which comprises irradiating a coated screen as claimed in claim 15 with actinic light, and then developing the insolubilised image.

* * * * *